United States Patent

Ryufuku et al.

[11] Patent Number: 6,060,261
[45] Date of Patent: May 9, 2000

[54] LUMINESCENCE METHOD FOR LUCIFERIN/LUCIFERASE SYSTEM AND LUMINESCENT REAGENT

[75] Inventors: Masayuki Ryufuku; Hozumi Tanaka; Hideyuki Takeuchi, all of Tokyo, Japan

[73] Assignee: Toyo Ink Mfg. Co., Ltd., Japan

[21] Appl. No.: 09/297,335

[22] PCT Filed: Aug. 28, 1998

[86] PCT No.: PCT/JP98/03833

§ 371 Date: Apr. 30, 1999

§ 102(e) Date: Apr. 30, 1999

[87] PCT Pub. No.: WO99/11766

PCT Pub. Date: Mar. 11, 1999

[30] Foreign Application Priority Data

Sep. 1, 1997 [JP] Japan ................................. 9-235740

[51] Int. Cl.[7] ................................................ C12Q 1/66
[52] U.S. Cl. ............................................. 435/8; 435/4
[58] Field of Search ................................. 435/8, 4

[56] References Cited

U.S. PATENT DOCUMENTS 5,618,682  4/1997  Scheirer .................................. 435/8
5,866,348  2/1999  Scheirer .................................. 435/8

FOREIGN PATENT DOCUMENTS 1-141592   6/1989   Japan .
1-262791  10/1989   Japan .
10-28599   2/1998   Japan .

*Primary Examiner*—Louise N. Leary
*Attorney, Agent, or Firm*—Wenderoth, Lind & Ponack, L.L.P.

[57] ABSTRACT

A luminescence method for a luciferin/luciferase system which comprises reacting a luciferin solution containing an increased amount of dissolved carbon dioxide with luciferase; and a luciferase assay reagent comprising a luciferin solution containing an increased amount of dissolved carbon dioxide. Thus, a method of luminescent assay excellent in continuity and stability is provided as a substitute for the conventional luminescent luciferase assay featured by rapidity and high sensitivity.

6 Claims, No Drawings

LUMINESCENCE METHOD FOR LUCIFERIN/LUCIFERASE SYSTEM AND LUMINESCENT REAGENT

TECHNICAL FIELDS

The present invention relates to a luminescence method for luciferin/luciferase system, which stabilizes a luminescent reaction and a luciferase assay reagent. The luminescence method for luciferin/luciferase system and the luciferase assay reagent, provided by the present invention, can be applied to all assay systems using a luciferase enzyme as a reporter and signal.

BACKGROUND

In a luminescent reaction with luciferin/luciferase in vitro, conventionally, the luminescence pattern thereof is observed in a flash state. Therefore, it is impossible to measure the luminescent reaction accurately without using a device having a specific mechanism of injecting a reagent. However, K. V. Wood et al. has established a luminescence system having a relatively long half-life period of luminescence as long as 5 minutes. (Wood, K. V. Recent advantage and prospects for beetle luciferase as genetic reporters. In: Bioluminescence and Chemiluminescence current status. Proceeding of the VIth International Symposium on Bioluminescence and Chemiluminescence, Cambridge, September 1990. P.543. Ed. by P. Stanley and L. J. Kricka.). Owing to this, it has become possible to accurately measure a luminescence unit in a luciferin/luciferase system with a luminometer or a liquid scintillation counter which does not have an automatic reagent-injecting device. So, a reporter assay method wherein luciferase generated as a reporter in a culture cell is measured at a high sensitivity has been widely used. However, when the reporter assay method is used in a High Throughput screening for developing a medication, the luminescence half-life period of 5 minutes is insufficient. For example, for measuring many samples by using 96 wells, luminescent reagents must be added several times and measurement must be carried out each time. Like this, restrictions on operation and measurement exist.

Further, luciferin contained as a luminescent substrate in a luminescent reagent is apt to be oxidized in a solution during storage, to form an oxyluciferine. It is well-known that the oxyluciferin inhibits the enzyme reaction of a luciferase. Conventional luminescent reagents containing luciferin as a luminescent substrate have a big problem that a luminescent activity deteriorates due to the oxidation of the luciferin. This problem prevents the further expansion of uses for the assay using luciferase as a reporter. Therefore, the development of a new stabilization method is expected.

It is an object of the present invention to provide a luminescence method for luciferin/luciferase system, which extends the half-life period of a luminescent reaction, and a luciferase assay reagent.

It is an another object of the present invention to a luminescence method for luciferin/luciferase system, which prevents the deterioration of a luminescent activity and gives a stable luminescence reaction, and a Luciferase assay reagent.

DISCLOSURE OF THE INVENTION

According to the present invention, there is provided a luminescence method for luciferin/luciferase system, which comprises reacting luciferin solution containing an increased amount of dissolved carbon dioxide with luciferase.

According to the present invention, further, there is provided a luminescence method for luciferin/luciferase system, wherein the pH of the luciferin solution is adjusted in the range of from 5.0 to 8.5.

According to the present invention, further, there is provided a luminescence method for luciferin/luciferase system, wherein the amount of the dissolved carbon dioxide in the luciferin solution is increased by adding a dry ice.

According to the present invention, further, there is provided a luminescence method for luciferin/luciferase system, wherein the amount of the dissolved carbon dioxide in the luciferin solution is increased by introducing a carbon dioxide gas.

According to the present invention, further, there is provided a luciferase assay reagent which comprises a luciferin solution containing an increased amount of dissolved carbon dioxide.

According to the present invention, further, there is provided a luciferase assay reagent which comprises a first component containing a dried luciferin and a second component of a solution containing an increased amount of dissolved carbon dioxide.

PREFERRED EMBODIMENT OF THE INVENTION

In the present invention, the term "luciferase" refers to all luciferases concerning a bioluminescence, such as a firefly.luciferase, a renilla.luciferase and a cypridina hilgendorfii.luciferase.

In the present invention, the term "luciferin" refers to luminescent substrates corresponding to luciferases concerning a bioluminescence, such as a firefly.luciferase, a renilla.luciferase and a cypridina hilgendorfii.luciferase.

As a method of increasing the amount of dissolved carbon dioxide in a luciferin solution as a luminescent reagent for a luciferase in the present invention, a method of adding a carbon dioxide gas or a dry ice is preferred. Examples of the method include even a method wherein an inorganic compound, such as sodium bicarbonate, which generates a gas by adding it into water, is added. However, it is preferred to use a carbon dioxide gas or a dry ice which scarcely impairs living things such as microorganism and which does not generate a chemical reaction or the like.

Owing to the use of a carbon dioxide gas, the luminescence reaction of luciferase is continued for a long time. Concurrently, a luminescence substrate, luciferin, in the solution can be protected from oxidation deterioration due to dissolved oxygen.

For controlling the pH of a luminescence solution, in the present invention, an inorganic acid such as hydrochloric acid, sulfuric acid, phosphoric acid and boric acid, an organic acid such as acetic acid, tartaric acid, malic acid, propionic acid, mucic acid, benzoic acid, maleic acid, succinic acid or fumaric acid, an inorganic alkaline compound such as sodium hydroxide, potassium hydroxide, aqueous ammonia, sodium carbonate and potassium carbonate, or an organic base such as aniline, pyridine, imidazole, monomethylamine, dimethylamine, trimethylamine, monoethylamine, diethylamine, triethylamine, ethanol amine, diethanol amine or triethanol amine, is added. By controlling a pH at a preferable pH value of pH 5 to 8.5, the shift to an alkaline side is prevented during a luminescence reaction, which can serve to maintain the enzyme activity of luciferase.

The luminescence reaction is extremely prevented when the pH value is beyond the range of 5.0 to 8.5. When the pH is high within the above range, a strong luminescence unit can be obtained. However, the half-life period is shortened. In contrast, when the pH is low, the luminescence unit is small. However, a long half-life period can be obtained. That is, the combination variation of pH and a buffer component thereof can adjust luminescence unit and the half-life period of luminescence to some extent when a luminescence solution of the same composition is used. The buffer solution component of controlling a pH, may be any one unless it does not prevent a luciferase activity. The buffer solution includes general buffer solutions such as tris-sulfate, citric acid and succinic acid, Good's buffer solutions such as HEPES and MES and broad buffer solutions such as GTA. The concentration of the buffer component may be any concentration unless it can sufficiently maintain a pH in the predetermined range from the initiation of luminescence to a time when the luminescence is reduced by half.

The luciferase assay reagent of the present invention is prepared so as to initiate a reaction at mixing it with a sample containing luciferase and to have a concentration of a component concerning a luminescence reaction, such as a luminescence substrate, which concentration is sufficient for emitting a lucifecase to be measured. The luminescence reagent includes a kit of a frozen product and a kit of a freeze-dried product.

The frozen product is obtained by freezing a component containing luciferin, ATP, CoA, a buffer solution component, magnesium ions, etc. Carbon dioxide is forcedly dissolved into a solution before the freezing. The frozen product is stored at about −70° C. After the frozen product thaws out and reaches room temperature fully, it is used.

The kit of the freeze-dried product comprises a first component obtained by freeze-drying a solution containing luciferin, ATP and CoA and a second component of a solution containing a buffer solution component and magnesium ions. The first component and the second component are mixed right before use. In this case, carbon dioxide is forcedly dissolved into the solution of the second component and stored with sealed. The freeze-dried product and the solution component are freeze-stored. After the freeze-dried product and the solution component thaw out and reach room temperature, these components are mixed before use.

Each of the frozen product and the freeze-dried product can be stored in a solution state for 24 hours at room temperature or for a month at low temperatures (4° C.) with almost no loss of luminescence properties.

The present invention will be explained more in detail with reference to Examples.

EXAMPLE 1

To 10 ml of a luciferse assay regent of "Pica Gene Luminescence Kit" (product No. "PGL100", supplied by TOYO INK MFG. Co., LTD), a GTA buffer solution whose pH was adjusted at 6.7 was added so as to have an end concentration of 100 mM. Then, a dry ice was added in an amount of 1 g per 10 ml of the luminescence reagent and the dry ice was completely vaporized. As a stabilizer for luciferase, glycerol was added so as to have an end concentration of 1%, and the mixture was mixed well to prepare a luminescence solution.

10 $\mu$l of an enzyme solution containing 100 ng/ml of luciferase was taken onto a measurement cuvette for a luminometer ("LB9506", supplied by Berthold). Then, 100 $\mu$l of the above prepared luminescence solution was added, and immediately, the cuvette was set on the luminometer. Luminescence units with the passage of time were measured from right after the addition of the reagent (0 minute) to after seven hours (420 minutes). In the luminescence reaction by the above luminescence reagent, the luminescence unit (RLU/sec) was stabilized at an approximately constant value after 5 minutes from the initiation, though the luminescence unit was in the increasing direction. 30 minutes after the initiation, the luminescence unit reached its peak and, then, it was gradually attenuated. Thereafter, two hours after the initiation, the luminescence unit came to 50% of the maximum luminescence unit, to reach a half-life period.

Further, when the luciferase enzyme solution was diluted and the diluted solution in the range of 10 ng ($10^{-9}$ g) to 1 fg ($10^{-15}$ g) was added, 10 fg of luciferase enzyme was detected the above luminescence solution.

Further, the prepared luminescence solution was frozen and defrosted three times. Almost no reduction of a luminescence activity was observed. The prepared luminescence solution after 1-month storage at 4° C. showed no activity reduction.

EXAMPLE 2

To 10 ml of a luciferase assay regent of "Pica Gene Luminescence Kit" (product No. "PGL100", supplied by TOYO INK MFG. Co., LTD), a citric acid buffer solution whose pH was adjusted at 6.3 was added so as to have an end concentration of 100 mM. Then, a dry ice was added in an amount of 1 g per 10 ml of the luminescence reagent and the dry ice was completely vaporized. As a stabilizer for luciferase, glycerol was added so as to have an end concentration of 1%, and the mixture was mixed well to prepare a luminescence solution.

10 $\mu$l of an enzyme solution containing 100 ng/ml of luciferase was taken onto a measurement cuvette for a luminometer ("LB9506", supplied by Berthold). Then, 100 $\mu$l of the above prepared luminescence solution was added, and immediately, the cuvette was set on the luminometer. Luminescence units with the passage of time were measured from right after the addition of the reagent (0-minute) to after seven hours (420 minutes). In the luminescence reaction by the above luminescence reagent, the luminescence unit (RLU/sec) was stabilized at an approximately constant value after 10 minutes from the initiation. 60 minutes after the initiation, the luminescence unit reached its peak and, then, it was gradually attenuated. Even after 7 hours, the luminescence unit was maintained at 67% of the maximum luminescence unit.

Further, when the luciferase enzyme solution was diluted and the diluted solution in the range of 10 ng to 1 fg was added, 100 fg of luciferase enzyme was detected with the above luminescence solution.

Further, the prepared luminescence solution was frozen and defrosted three times. Almost no reduction of a luminescence activity was observed. The prepared luminescence solution after 1-month storage at 4° C. showed no activity reduction.

EXAMPLE 3

To 10 ml of a luciferse assay regent of "Pica Gene Luminescence Kit" (product No. "PGL100", supplied by TOYO INK MFG. Co., LTD), a GTA buffer solution whose pH was adjusted at 6.7 was added so as to have an end concentration of 100 mM. Then, a carbon dioxide gas was introduced into the reagent solution with a gas introducing tube at a flow rate of 20 ml/min for about 3 minutes while bubbling lightly. As a stabilizer for luciferase, glycerol was added so as to have an end concentration of 1%, and the mixture was mixed well to prepare a luminescence solution.

10 μl of an enzyme solution containing 100 ng/ml of luciferase was taken onto a measurement cuvette for a luminometer ("LB9506", supplied by Berthold). Then, 100 μl of the above prepared luminescence solution was added, and immediately, the cuvette was set on the luminometer. Luminescence units with the passage of time were measured from right after the addition of the reagent (0 minute) to after seven hours (420 minutes). In the luminescence reaction by the above luminescence reagent, the luminescence unit (RLU/sec) was stabilized at an approximately constant value after 5 minutes from the initiation, though the luminescence unit was in the increasing direction. 30 minutes after the initiation, the luminescence unit reached its peak and, then, it was gradually attenuated. Thereafter, two hours after the initiation, the luminescence unit came to 50% of the maximum luminescence unit, to reach a half-life period.

Further, when the luciferase enzyme solution was diluted and the diluted solution in the range of 10 ng to 1 fg was added, 10 fg of luciferase enzyme was detected with the above luminescence solution.

Further, the prepared luminescence solution was frozen and defrosted three times. Almost no reduction of a luminescence activity was observed. The prepared luminescence solution after 1-month storage at 4° C. showed no activity reduction.

Comparative Example 1

10 μl of an enzyme solution containing 100 ng/ml of luciferase was taken onto a measurement cuvette for a luminometer ("LB9506", supplied by Berthold). "Pica Gene Luminescence Kit" (product No. "PGL100", supplied by TOYO INK MFG. Co., LTD) was prepared as a conventional luminescence reagent. 100 μm of the prepared reagent is added to the cuvette. Immediately, the cuvette was set on the luminometer. Luminescence units with the passage of time were measured from right after the addition of the reagent (0-minute) to after seven hours (420 minutes). From the initiation of the luminescence reaction, very high luminescence units were obtained. However, the luminescence unit reached a half-life period after about 5 minutes. 2 hours after the initiation of the reaction, the luminescence unit was reduced to 1.4% of the maximum luminescence unit (RLU/sec). Further, 7 hours after the initiation, it was reduced to 0.7% of the maximum luminescence unit (RLU/sec). When the prepared luminescence solution was frozen and defrosted three times, the luminescence activity was reduced to 90%. The luminescence solution after 1-month storage at 4° C. was reduced in activity to 10% or less.

Table 1 shows the measured results in Examples and Comparative Example. The method of the present invention shows superior results in continuation and stability of luminescence to those of the conventional method.

TABLE 1

| | Variations of luminescence unit with the passage of time and retaining ratios of luminescence unit | | | |
|---|---|---|---|---|
| Hours passed | CEx.1 | Ex.1 | Ex.2 | Ex.3 |
| 0 hour | 2,270,882 | 698,851 | 44,725 | 701,274 |
| | 100% | 100% | 100% | 100% |

TABLE 1-continued

| | Variations of luminescence unit with the passage of time and retaining ratios of luminescence unit | | | |
|---|---|---|---|---|
| Hours passed | CEx.1 | Ex.1 | Ex.2 | Ex.3 |
| 0.5 hour | 689,060 | 716,254 | 42,541 | 712,527 |
| | 30.3% | 102.5% | 95.1% | 101.6% |
| 1 hour | 149,067 | 581,821 | 42,839 | 582,496 |
| | 6.6% | 83.3% | 95.8% | 83.1% |
| 2 hours | 31,283 | 357,833 | 40,710 | 358,285 |
| | 1.4% | 51.2% | 91.0% | 51.1% |
| 3 hours | 17,178 | 200,816 | 38,503 | 201,224 |
| | 0.8% | 28.7% | 86.1% | 28.7% |
| 5 hours | 7,433 | 79,764 | 33,771 | 80,012 |
| | 0.3% | 11.4% | 75.5% | 11.4% |
| 8 hours | 3,935 | 38,641 | 28,940 | 38,851 |
| | 0.2% | 5.5% | 64.7% | 5.5% |

Note; 100 μl of each luminescence reagent was added to 1 ng/10 μl of a luciferase solution, luminescence units with time from right after the reaction initiation were measured with a luminometer ("LB9506", supplied by Berthold), to measure a relative luminescence unit per unit second (RLU/s).

UTILITIES IN INDUSTRY

When the luminescence solution prepared by the present invention is used, stability in luminescence is remarkably increased as compared with the conventional one having a half-life period of luminescence of 5 minutes. When the luminescence solution having a high pH is used, the half-life period is increased by 20 times or more at a detection sensitivity of 10 fg. When the luminescence solution having a low pH is used, the half-life period is increased by 90 times or more at a detection sensitivity of 100 fg.

As described above, according to the present invention, there is provided a luminescence measuring method excellent in continuation and stability instead of the conventional luminescence measuring method of luciferase, which method is featured by rapidity and high sensitivity.

What is claimed is:

1. A luminescence method for luciferin/luciferase system, which comprises reacting luciferin solution containing an increased amount of dissolved carbon dioxide with luciferase.

2. The luminescence method according to claim 1, wherein the pH of the luciferin solution is adjusted in the range of from 5.0 to 8.5.

3. The luminescence method according to claim 1, wherein the amount of the dissolved carbon dioxide in the luciferin solution is increased by adding a dry ice.

4. The luminescence method according to claim 1, wherein the amount of the dissolved carbon dioxide in the luciferin solution is increased by introducing a carbon dioxide gas.

5. A luciferase assay reagent which comprises a luciferin solution containing an increased amount of dissolved carbon dioxide.

6. A luciferase assay reagent which comprises a first component containing a dried luciferin and a second component of a solution containing an increased amount of dissolved carbon dioxide.

* * * * *